(12) United States Patent
Kohl et al.

(10) Patent No.: US 7,301,030 B2
(45) Date of Patent: Nov. 27, 2007

(54) PROCESS FOR PREPARING (S)-PANTOPRAZOLE

(75) Inventors: Bernhard Kohl, Konstanz (DE); Bernd Müller, Konstanz (DE); Ralf Steffen Weingart, Konstanz (DE)

(73) Assignee: Nycomed GmbH, Konstanz (DE)

( * ) Notice: Subject to any disclaimer, the term of this patent is extended or adjusted under 35 U.S.C. 154(b) by 0 days.

(21) Appl. No.: 10/536,891

(22) PCT Filed: Dec. 3, 2003

(86) PCT No.: PCT/EP03/13604

§ 371 (c)(1),
(2), (4) Date: Nov. 25, 2005

(87) PCT Pub. No.: WO2004/052881

PCT Pub. Date: Jun. 24, 2004

(65) Prior Publication Data

US 2006/0167262 A1    Jul. 27, 2006

(30) Foreign Application Priority Data

Dec. 6, 2002  (EP) .................... 02027274
Aug. 29, 2003 (DE) .................... 103 40 254

(51) Int. Cl.
*C07D 401/12* (2006.01)
(52) U.S. Cl. .................................. 546/273.7
(58) Field of Classification Search ............. 546/273.7
See application file for complete search history.

(56) References Cited

U.S. PATENT DOCUMENTS 5,948,789 A    9/1999  Larsson et al.

FOREIGN PATENT DOCUMENTS

| EP | 0 005 129 B1 | 10/1979 |
|----|--------------|---------|
| EP | 0 166 287 B1 | 1/1986 |
| EP | 0 174 726 B1 | 3/1986 |
| EP | 0 268 956 B2 | 6/1988 |
| WO | 91/12221 A1 | 8/1991 |
| WO | 92/08716 | 5/1992 |
| WO | 94/24867 A1 | 11/1994 |
| WO | 94/25028 A1 | 11/1994 |
| WO | 94/27988 A1 | 12/1994 |
| WO | 96/02535 A1 | 2/1996 |
| WO | 96/17076 A1 | 6/1996 |
| WO | 96/17077 A1 | 6/1996 |
| WO | 97/02261 A1 | 1/1997 |
| WO | 99/47514 A1 | 9/1999 |
| WO | 2004/052882 A1 | 6/2004 |

OTHER PUBLICATIONS

Bonchio, M., et al., "The First Chiral Zirconium (IV) Catalyst For Highly Stereoselective Sulfoxidation", *J. Org. Chem.* vol. 64, No. 4, pp. 1326-1330, (1999).

Ikegami, S., et al., "Asymmetric Epoxidation Of Homoallylic Alcohols Using Zirconium Tetrapropoxide, Dicyclohexyltartramide, And t-Butyl Hydroperoxide System", *Chemistry Letters*, pp. 83-84, (1987).

Nugent, W.A., "Chiral Lewis Acid Catalysis. Enantioselective Addition Of Azide To Meso Epoxides", *J. Am. Chem. Soc.*, vol. 114, No. 7, pp. 2768-2769, (1992).

*Primary Examiner*—Patricia L. Morris
(74) *Attorney, Agent, or Firm*—The Nath Law Group; Joshua B. Goldberg; Sheldon M. McGee

(57) ABSTRACT

The invention relates to a novel process for preparing (S)-pantoprazole using a chiral zirconium complex or a chiral hafnium complex.

20 Claims, No Drawings

PROCESS FOR PREPARING (S)-PANTOPRAZOLE

SUBJECT-MATTER OF THE INVENTION

The present invention relates to a novel process for preparing the active compound (S)-pantoprazole which can be used for preparing medicaments in the pharmaceutical industry.

TECHNICAL BACKGROUND

Pyridin-2-ylmethylsulphinyl-1H-benzimidazoles and compounds of a closely related structure, as known, for example, from EP-A-0005129, EP-A-0166287, EP-A-0174726 and EP-A-0268956, are, owing to their $H^+/K^+$-ATPase-inhibitory action, of considerable importance in the therapy of diseases associated with an increased secretion of gastric acid.

Examples of active compounds from this class of compounds which are commercially available or in clinical development are 5-methoxy-2-[(4-methoxy-3,5-dimethyl-2-pyridinyl)methylsulphinyl]-1H-benzimidazole (INN: omeprazole), (S)-5-methoxy-2-[(4-methoxy-3,5-dimethyl-2-pyridinyl)methyl-sulphinyl]-1H-benzimidazole (INN: esomeprazole), 5-difluoromethoxy-2-[(3,4-dimethoxy-2-pyridinyl)methylsulphinyl]-1H-benzimidazole (INN: pantoprazole), 2-[3-methyl-4-(2,2,2-trifluoroethoxy)-2-pyridinyl)methylsulphinyl]-1H-benzimidazole (INN: lansoprazole), 2-{[4-(3-methoxypropoxy)-3-methylpyridin-2-yl]methylsulphinyl}-1H-benzimidazole (INN: rabeprazole) and 5-methoxy-2-((4-methoxy-3,5-dimethyl-2-pyridylmethyl)sulphinyl)-1H-imidazo[4,5-b]pyridine (INN: tenatoprazole).

The abovementioned sulphinyl derivatives which, owing to their mechanism of action, are also referred, to as proton pump inhibitors or abbreviated PPI are chiral compounds. The process usually used for preparing the PPI is the oxidation of the corresponding sulphides. This oxidation gives—unless particular measures are taken—a racemic mixture comprising about the same proportions of the two enantiomers (stereoisomers), i.e. the (+)- and (−)-form or the (R)- and (S)-form of the PPI.

Since enantiomers are thermally relatively stable, i.e. they do not racemize on storage—in particular in solid form—there has in the past been no lack of efforts to separate PPI enantiomer mixtures or to prepare the PPI enantiomers in more or less pure form.

PRIOR ART

The international patent application WO91/12221 describes a process for separating enantiomers using a cellulase enzyme. One of the active compounds mentioned as being separable into the enatiomers with the aid of this process is omeprazole.

The international patent application WO92/08716 describes, for the first time, a chemical process which allows the separation of pyridin-2-ylmethylsulphinyl-1H-benzimidazoles into their optical isomers. Compounds mentioned as having been prepared in an exemplary manner are, inter alia, the compounds (+)-5 and (−)-5-difluoromethoxy-2-[(3,4-dimethoxy-2-pyridinyl)methylsulphinyl]-1H-benzimidazole [=(+)- and (−)-pantoprazole]. The international patent application WO92/08716 refers to the fact that the optical isomers of the pyridin-2-yl-methylsulphinyl-1H-benzimidazoles, i.e. the (+)- and (−)-enantiomers or the (R)- and (S)-enantiomers, are used as active compounds in medicaments for the treatment of gastrointestinal disorders. With respect to the mode of application and the dosage of the active compounds, reference is made inter alia to the European patent 166 287.

The international patent application WO94/27988 describes the separation of racemic omeprazole into the enantiomers, using chiral auxiliaries.

The international patent application WO96/02535 (=U.S. Pat. No. 5,948,789) describes a process for the enantioselective synthesis of PPI using chiral titanium complexes. What is described is, inter alia, the synthesis of (+)- and (−)-[or, expressed in a different way, (R)- and (S)]-pantoprazole, the chiral auxiliary used for the synthesis of (+)-pantoprazole being diethyl (+)-tartrate and the chiral auxiliary used for the preparation of (−)-pantoprazole being diethyl (−)-tartrate.

The international patent applications WO96/17076 and WO96/17077 describe the enantioselective biooxidation or bioreduction with the use of certain microorganisms for the preparation of enantiomerically pure or enantiomerically enriched PPI.

The international patent application WO97/02261 describes the enrichment of PPI enantiomers by selective precipitation.

The international patent applications WO94/24867 and WO94/25028 claim the use of the compounds (−)- and (+)-pantoprazole for treating stomach disorders in humans. Each of the stereoisomers is said to have medical advantages compared to the respective other stereoisomers.

The enantioselective sulphoxidation for preparing esomeprazole ((S)-omeprazole) on a large scale using a chiral titanium complex is described in *Tetrahedron, Asymmetry*, (2000), 11, 3819-3825.

The enantioselective sulphoxidation of aryl alkyl sulphides and dialkyl sulphides in the presence of a zirconium catalyst having a polydentate ligand is described in *J. Org. Chem.*, (1999), 64(4), 1327.

DESCRIPTION OF THE INVENTION

The invention provides a process for preparing (−)- or (S)-pantoprazole. The process is characterized in that the oxidation of the corresponding sulphide is carried out in the presence of a chiral zirconium complex or a chiral hafnium complex, the chiral auxiliary used being a (+)-L-tartaric acid derivative.

The fact that, when a chiral zirconium complex or a chiral hafnium complex is used for preparing (−)- or (S)-pantoprazole, it is possible to use, as chiral auxiliary, preferably a (+)-L-tartaric acid derivative instead of a (−)-D-tartaric acid derivative is surprising and particularly advantageous, since (+)-L-tartaric acid derivatives—with respect to naturally considerably more frequently occurring (+)-L-tartaric acid—are considerably less expensive and as a consequence highly suitable in particular for a preparation on an industrial scale.

The oxidation is advantageously carried out in an organic solvent, such as, for example, ethyl acetate, toluene, dichloromethane, dioxane or, preferably, methyl isobutyl ketone, where it is not necessary for the solvents mentioned to be completely anhydrous or where anhydrous solvents are in each case optionally admixed with a defined proportion of water, for example up to a maximum of 0.5 equivalent. For reactions with less than 0.5 equivalent of zirconium or hafnium complex, it is preferred to use an anhydrous solvent. The solvents employed may be used in the commericially available quality.

A solvent essentially comprises a specific solvent if it contains at least 50%, preferably at least 90%, in particular at least 95%, of the said specific solvent. An anhydrous solvent is essentially free of water, having a water content of less than 5%, preferably less than 1%, in particular less than 0.3%.

Suitable oxidizing agents are all anhydrous oxidizing agents customarily used for the synthesis of PPI, where particular mention may be made of hydroperoxides, such as, for example, tert-butyl hydroperoxide or, in particular, cumene hydroperoxide. In general, 0.90 to 1.3 oxidation equivalents, preferably 0.95-1.05 equivalents, of the oxidizing agent are used.

Suitable zirconium complexes are, for example, zirconium(IV) acetylacetonate, zirconium(IV) butoxide, zirconium(IV) tert-butoxide, zirconium(IV) ethoxide and, in particular, zirconium(IV) n-propoxide (preferably as a solution in n-propanol) or zirconium(IV) isopropoxide (preferably in the form of the zirconium(IV) isopropoxide/isopropanol complex). Suitable hafnium complexes are, for example, hafnium(IV) acetylacetonate, hafnium(IV) butoxide, hafnium(IV) n-propoxide, hafnium(IV) isopropoxide (preferably in the form of the hafnium(IV) isopropoxide/isopropanol complex), hafnium(IV) ethoxide and in particular hafnium(IV) tert-butoxide. Preference is given to using a zirconium complex.

In general, 0.01-2 equivalents, preferably 0.05-0.9 equivalent, of the zirconium complex or of the hafnium complex are used.

Suitable (+)-L-tartaric acid derivatives are, for example, tartaric acid amides, such as (+)-L-tartaric acid bis-(N,N-diallylamide), (+)-L-tartaric acid bis-(N,N-dibenzylamide), (+)-L-tartaric acid bis-(N,N-diisopropylamide), (+)-L-tartaric acid bis-(N,N-dimethylamide), (+)-L-tartaric acid bis-(N-pyrrolidinamide, (+)-L-tartaric acid bis-(N-piperidinamide), (+)-L-tartaric acid bis-(N-morpholinamide), ((+))-L-tartaric acid bis-(N-cycloheptylamide) or (+)-L-tartaric acid bis-(N-4-methyl-N-piperazinamide), or dialkyl tartrates, such as dibutyl (+)-L-tartrate, di-tert-butyl (+)-L-tartrate, diisopropyl (+)-L-tartrate, dimethyl (+)-L-tartrate and diethyl (+)-L-tartrate. In general, 0.024 equivalents, preferably 0.1-2 equivalents, of the (+)-L-tartaric acid derivative are employed.

Particularly preferred tartaric acid derivatives are (+)-L-tartaric acid bis-(N,N-dimethylamide), (+)-L-tartaric acid bis-(N-pyrrolidinamide), (+)-L-tartaric acid bis-(N-morpholinamide).

The oxidation is preferably carried out at temperatures between −20 and 50° C., in particular at room temperature, and optionally in the presence of a base, suitable bases being, in particular, organic bases, preferably a tertiary amine, such as triethylamine or N-ethyldiisopropylamine.

If the process is carried out in a suitable manner, (−)- or (S)-pantoprazole is obtained in an optical purity of >95%. By further steps, such as, for example, pH-controlled reprecipitation and/or recrystallization in a suitable solvent, such as, for example, isopropanol, it is possible to further increase the optical purity considerably. Reprecipitation is carried out via intermediate preparation of suitable salts, such as, for example, via the sodium salt (for other possible salts, see, for example, EP-A-166287).

The invention is illustrated in more detail by the examples below, but not limited in any way. The abbreviation h stands for hour(s).

EXAMPLES 1. (−)-5-Difluoromethoxy-2-[(3,4-dimethoxy-2-pyridinyl)methylsulphinyl]-1H-benzimidazole [=(−)-pantoprazole or (S)-pantoprazole] with diethyl (+)-L-tartrate and zirconium(IV) isopropoxide/isopropanol A) At room temperature, 20.2 g of 5-difluoromethoxy-2-[(3,4-dimethoxy-2-pyridinyl)methylthio]-1H-benzimidazole together with 17.9 g of diethyl (+)-tartrate, 13.4 g of zirconium(IV) isopropoxide/isopropanol and 0.1 ml of water are suspended in 100 ml of methyl isobutyl ketone. The mixture is heated at 40° C. for one hour, resulting in the formation of an almost clear solution. After cooling to room temperature, 4.1 ml of N-ethyldiisopropylamine are added. 11 ml of cumene hydroperoxide are then slowly metered in. Stirring at room temperature is continued until the oxidation process has ended (monitored by TLC). The clear solution is quenched with 0.9 g of sodium thiosulphate in 54 ml of water and 30.3 g of 40% (w/w) of NaOH and stirred for another 14 h. After addition of 25 g of sodium chloride, the phases are separated. The aqueous phase is extracted with 50 ml of methyl isobutyl ketone. The combined organic phases are washed together using 25 ml of saturated sodium chloride solution. 150 ml of water are added to the methyl isobutyl ketone solution, and the pH is adjusted to 13 using 10% (w/w) NaOH. The phases are separated and the methyl isobutyl ketone phase is extracted once more with 50 ml of water at pH 13. The aqueous phases are combined and, at 40° C. and under reduced pressure, subjected to incipient distillation. At 40-50° C., (−)-pantoprazole is precipitated by addition of 10% strength acetic acid to pH 9. Under pH control, stirring is continued for another 12 h. The beige crystals are filtered off and washed with 50 ml of water. This gives the title compound in an optical purity of >90%.

To increase the purity, (−)-pantoprazole is dissolved in water/NaOH and again precipitated by addition of acetic acid to pH 9. Drying gives a beige powder of melting point 145° C. (decomposition) and an optical purity of >95%. If this powder is recrystallized from 2-PrOH, a clear crystal of melting point 147-149° C. (decomposition) with an optical rotation of $\alpha_D^{20}$=−140 (c=0.5, MeOH) is obtained.

B) Alternatively, the reaction described in Example 1A can be carried out in 100 ml of toluene instead of methyl isobutyl ketone. If the reaction is carried out in toluene, the zirconium salts have to be filtered off after quenching and the reaction product ((S)-pantoprazole as sodium salt) is directly extracted into the aqueous phase. From the aqueous phase, it can then be precipitated under controlled pH as (S)-pantoprazole. This gives beige crystals of an optical purity of >95%.

2. (−)-5-Difluoromethoxy-2-[(3,4-dimethoxy-2-pyridinyl)methylsulphinyl]-1H-benzimidazole [=(−)-pantoprazole or (S)-pantoprazole] with (+)-L-tartaric acid bis-(N,N-dimethylamide) and zirconium (IV)isopropoxide/isopropanol At room temperature, 20.2 g of 5-difluoromethoxy-2-[(3,4-dimethoxy-2-pyridinyl)methylthio]-1H-benzimidazole are suspended in 100 ml of methyl isobutyl ketone together with 18.0 g of (+)-L-tartaric acid bis-(N,N-dimethylamide) and 13.4 g of zirconium(IV) isopropoxide-isopropanol. The mixture is heated at 40° C. for one hour, resulting in the formation of a solution which is almost clear. After cooling to room temperature, 4.1 ml of N-ethyldiisopropylamine are added. 11 ml of cumene hydroperoxide are then slowly metered in. The mixture is stirred at room temperature until the oxidation has ended (5-10 hours, monitored by TLC). The clear solution is diluted with 100 ml of methyl isobutyl ketone and quenched with 1.8 g of sodium thiosulphate in 140 ml of water and stirred for a further 14 hours. After phase separation, 55 ml of saturated sodium bicarbonate solution and 55 ml of methyl isobutyl ketone are added to the aqueous phase, and the phases are separated. Another 55 ml of saturated sodium bicarbonate solution and 55 ml of methyl isobutyl ketone are added to the aqueous phase, and the phases are separated. The combined methyl isobutyl ketone phases are then washed twice with 55 ml of saturated sodium bicarbonate solution. 150 ml of water are added to the methyl isobutyl ketone phase, and the pH is adjusted to pH=13 using a 40% by weight strength aqueous solution of sodium hydroxide. After phase separation, the methyl isobutyl ketone phase is extracted with another 50 ml of water at pH=13. The aqueous phases are combined and, at 40° C., subjected to incipient distillation under reduced pressure. At 40-45° C., (−)-pantoprazole is precipitated by addition of 10% strength acetic acid to pH=9.0. The mixture is stirred for another 12 hours during which the pH is monitored. The beige crystals are filtered off and washed with 50 ml of water. The title compound is obtained in a yield of about 15 g (73% of theory) and an optical purity of >95%.

To increase the purity, (−)-pantoprazole is dissolved in water/aqueous sodium hydroxide solution at pH=13 and re-precipitated with acetic acid (10%) at pH=9.0.

3. (−)-5-Difluoromethoxy-2-[(3,4-dimethoxy-2-pyridinyl)methylsulphinyl]-1H-benzimidazole [=(−)-pantoprazole or (S)-pantoprazole] with ((+))-L-tartaric acid bis-(N,N-pyrrolidinamide) and zirconium (IV) isopropoxide/isopropanol At room temperature, 20.2 g of 5-difluoromethoxy-2-[(3,4-dimethoxy-2-pyridinyl)methylthio]-1H-benzimidazole are suspended in 100 ml of methyl isobutyl ketone together with 22.6 g of (2R,3R)-(+)-L-tartaric acid bis-(N-pyrrolidinamide) and 13.4 g of zirconium(IV) isopropoxide-isopropanol. The mixture is heated at 40° C. for one hour, resulting in the formation of a solution which is almost clear. After cooling to room temperature, 4.1 ml of N-ethyldiisopropylamine are added. 11 ml of cumene hydroperoxide are then slowly metered in. The mixture is stirred at room temperature until the oxidation has ended (5-10 hours, monitored by TLC). The clear solution is diluted with 100 ml of methyl isobutyl ketone and quenched with 1.8 g of sodium thiosulphate in 140 ml of saturated sodium bicarbonate solution and stirred for a further 14 hours. After phase separation, the mixture is washed twice with 55 ml of saturated sodium bicarbonate solution. 150 ml of water are added to the methyl isobutyl ketone phase, and the pH is adjusted to pH=13 using a 40% by weight strength aqueous solution of sodium hydroxide. After phase separation, the methyl isobutyl ketone phase is extracted with another 50 ml of water at pH=13. The aqueous phases are combined and, at 40° C., subjected to incipient distillation under reduced pressure. At 40-45° C., (−)-pantoprazole is precipitated by addition of 10% strength acetic acid to pH=9.0. The mixture is stirred for another 12 hours during which the pH is monitored. The beige crystals are filtered off and washed with 50 ml of water. The title compound is obtained in a yield of about 17 g (80% of theory) and an optical purity of >98%.

To increase the purity, (−)-pantoprazole is dissolved in water/aqueous sodium hydroxide solution at pH=13 and re-precipitated with acetic acid (10%) at pH=9.0.

4. (−)-5-Difluoromethoxy-2-[(3,4-dimethoxy-2-pyridinyl)methylsulphinyl]-1H-benzimidazole [=(−)-pantoprazole or (S)-pantoprazole] with (+)-L-tartaric acid bis-(N,N-pyrrolidinamide) and zirconium (IV) n-propoxide At room temperature, 20.2 g of 5-difluoromethoxy-2-((3,4-dimethoxy-2-pyridinyl)methylthio]-1H-benzimidazole are suspended in 100 ml of methyl isobutyl ketone together with 22.6 g of (+)-L-tartaric acid bis-(N-pyrrolidinamide) and 16.5 g of zirconium(IV) n-propoxide (70% in propanol). The mixture is heated at 40° C. for one hour, resulting in the formation of a solution which is almost clear. After cooling to room temperature, 4.1 ml of N-ethyldiisopropylamine are added. 10 ml of cumene hydroperoxide are then slowly metered in. The mixture is stirred at room temperature until the oxidation has ended (5-24 hours, monitored by TLC). The clear solution is diluted with 100 ml of methyl isobutyl ketone and quenched with 1.8 g of sodium thiosulphate in 140 ml of saturated sodium bicarbonate solution and stirred for a further 14 hours. After phase separation, the mixture is washed twice with 55 ml of saturated sodium bicarbonate solution. 150 ml of water are added to the methyl isobutyl ketone phase, and the pH is adjusted to pH=13 using a 40% by weight strength aqueous solution of sodium hydroxide. After phase separation, the methyl isobutyl ketone phase is extracted with another 50 ml of water at pH=13. The aqueous phases are combined and, at 40° C., subjected to incipient distillation under reduced pressure. At 40-45° C., (−)-pantoprazole is precipitated by addition of 10% strength acetic acid to pH=9.0. The mixture is stirred for another 12 hours during which the pH is monitored. The beige crystals are filtered off and washed with 50 ml of water. The title compound is obtained in a yield of about 16 g (75% of theory) and an optical purity of >98%.

To increase the purity, (−)-pantoprazole is dissolved in water/aqueous sodium hydroxide solution at pH=13 and re-precipitated with acetic acid (10%) at pH=9.0.

5. (−)-5-Difluoromethoxy-2-[(3,4-dimethoxy-2-pyridinyl)methylsulphinyl]-1H-benzimidazole [=(−)-pantoprazole or (S)-pantoprazole] with (+)-L-tartaric acid bis-(N,N-pyrrolidinamide) and zirconium (IV) n-propoxide Analogously to Example 4, reaction of 5-difluoromethoxy-2-[(3,4-dimethoxy-2-pyridinyl)methylthio]-1H-benzimidazole under otherwise identical conditions, but without addition of N-ethyldiisopropylamine, gives the title compound in a yield of 65% of theory and an optical purity of >98%.

6. (−)-5-Difluoromethoxy-2-[(3,4-dimethoxy-2-pyridinyl)methylsulphinyl]-1H-benzimidazole [=(−)-pantoprazole or (S)-pantoprazole] with catalytic amounts of (+)-L-tartaric acid bis-(N-pyrrolidinamide) and zirconium(IV) n-propoxide Analogously to Example 4, reaction of 5-difluoromethoxy-2-[(3,4-dimethoxy-2-pyridinyl)methylthio]-1H-benzimidazole under otherwise identical conditions, but with 0.1 equivalent of zirconium n-propoxide, 0.25 equivalent of (+)-L-tartaric acid bis-(N-pyrrolidinamide) and 0.07 equivalents of Hünig base gives, after an oxidation time of 48-72 h, the title compound in a yield of 80% of theory and an optical purity of >98%.

7. (−)-5-Difluoromethoxy-2-[(3,4-dimethoxy-2-pyridinyl)methylsulphinyl]-1H-benzimidazole [=(−)-pantoprazole or (S)-pantoprazole] with catalytic amounts of (+)-L-tartaric acid bis-(N-pyrrolidinamide) and zirconium(IV) n-propoxide At room temperature, 50.0 g of 5-difluoromethoxy-2-[(3,4-dimethoxy-2-pyridinyl)methylthio]-1H-benzimidazole and 5.2 g of (+)-L-tartaric acid bis-(N-pyrrolidinamide) (0.15 eq.) are suspended in 360 ml of methyl isobutyl ketone (MIBK). The suspension is heated at 40-45° C. and 60 ml of MIBK are distilled off for azeotropic removal of water present in the mixture. At this temperature, 3.2 g of zirconium(IV) n-propoxide (70% in propanol, 0.05 eq.) are added, and the mixture is stirred for 1 hour. After cooling to 30° C., 0.9 ml of N-ethyldiisopropylamine are added. 27.1 g of cumene hydroperoxide (80% in cumene) are then slowly metered in. Stirring is continued at 30° C. until the exothermic oxidation process has ended (20 hours, monitored by TLC or HPLC). The suspension is diluted with 60 ml of 2-propanol and quenched with 1.69 g of sodium thiosulphate in 100 ml of saturated sodium bicarbonate solution and stirred for at least 2 hours. After phase separation, the mixture is washed twice with 50 ml of saturated sodium bicarbonate solution. 150 ml of water are added to the methyl isobutyl ketone phase, and the pH is adjusted to 12.5-13 using 10 ml of aqueous sodium hydroxide solution (40% (w/w)). After phase separation, the methyl isobutyl ketone phase is extracted 2 more times with 100 ml of water and 2 ml of aqueous sodium hydroxide solution (40% (w/w)) at pH=12.5-13. The combined aqueous phases are reextracted twice with 50 ml of methyl isobutyl ketone and subjected to incipient distillation at 40° C. under reduced pressure. At 40-45° C., (−)-pantoprazole is precipitated by addition of 10% strength acetic acid to pH=9.0. Under pH control, stirring is continued for another 12 hours. The beige crystals are filtered off and washed twice with 50 ml of water.

This gives the title compound in a yield of 82% of theory in a chemical purity of 95% and an optical purity of >95%.

To increase the purity, (−)-pantoprazole is dissolved in water/aqueous sodium hydroxide solution at pH=13 and again precipitated at pH=9.0 using acetic acid (10%). This gives the title compound in a yield of 75% of theory in a chemical purity of >97% and an optical purity of >98%.

8. (−)-5-Difluoromethoxy-2-[(3,4-dimethoxy-2-pyridinyl)methylsulphinyl]-1H-benzimidazole [=(−)-pantoprazole or (S)-pantoprazole] with catalytic amounts of (+)-L-tartaric acid bis-(N-pyrrolidinamide) and zirconium(IV) isopropoxide/isopropanol At room temperature, 10.0 g of 5-difluoromethoxy-2-[(3,4-dimethoxy-2-pyridinyl)methylthio]-1H-benzimidazole and 1.05 g of (+)-L-tartaric acid bis-(N-pyrrolidinamide) (0.15 eq.) are suspended in 72 ml of methyl isobutyl ketone. The suspension is heated at 40-45° C. and 12 ml of MIBK are distilled off for azeotropic removal of water present in the mixture. At this temperature, 0.53 g of zirconium(IV) isopropoxide isopropanol (0.05 eq.) is added and the mixture is stirred for 1 hour. After cooling to 30° C., 0.16 ml of N-ethyldiisopropylamine is added. 5.5 g of cumene hydroperoxide (80% in cumene) are then slowly metered in. Stirring is continued at 30° C. until the exothermic oxidation process has ended (20 hours, monitored by TLC or HPLC). HPLC of the reaction shows 82% of title compound in an optical purity of >95%.

9. (−)-5-Difluoromethoxy-2-[(3,4-dimethoxy-2-pyridinyl)methylsulphinyl]-1H-benzimidazole [=(−)-pantoprazole or (S)-pantoprazole] with catalytic amounts of (+)-L-tartaric acid bis-(N-pyrrolidinamide) and zirconium(IV) n-propoxide At room temperature, 50.0 g of 5-difluoromethoxy-2-[(3,4-dimethoxy-2-pyridinyl)methylthio]-1H-benzimidazole and 13.9 g of (+)-L-tartaric acid bis-(N-pyrrolidinamide) (0.40 eq.) are suspended in 360 ml of methyl isobutyl ketone. The suspension is heated at 40-45° C. and 60 ml of MIBK are distilled off for azeotropic removal of water present in the mixture. At this temperature, 6.4 g of zirconium(IV) n-propoxide (70% in propanol, 0.10 eq.) are added, and the mixture is stirred for 1 hour. After cooling to 30° C., 1.8 ml of N-ethyldiisopropylamine are added. 27.1 g of cumene hydroperoxide (80% in cumene) are then slowly metered in. Stirring is continued at 30° C. until the exothermic oxidation process has ended (20 hours, monitored by TLC or HPLC: chemical purity: 90% of pantoprazole sulphoxide). The suspension is diluted with 120 ml of 2-propanol and quenched with 1.69 g of sodium thiosulphate in 100 ml of saturated sodium bicarbonate solution and stirred for at least 2 hours. After phase separation, the mixture is washed twice with 50 ml of saturated sodium bicarbonate solution. 350 ml of water are added to the methyl isobutyl ketone phase, and the pH is adjusted to 12.5-13 using 10 ml of aqueous sodium hydroxide solution (40% (w/w)). After phase separation, the methyl isobutyl ketone phase is extracted 2 more times with 100 ml of water and 2 ml of aqueous sodium hydroxide solution (40% (w/w)) at pH=12.5-13. The combined aqueous phases are reextracted twice with 50 ml of methyl isobutyl ketone and subjected to incipient distillation at 40° C. under reduced pressure. At 40-45° C., (−)-pantoprazole is precipitated by addition of 10% strength acetic acid to pH=9.0. Under pH control, stirring is continued for another 12 hours. The beige crystals are filtered off and washed twice with in each case 50 ml of water.

This gives the title compound in a yield of 85% of theory in a chemical purity of 95% and an optical purity of >95%. To increase the purity, (−)-pantoprazole is dissolved in water/aqueous sodium hydroxide solution at pH=13 and again precipitated at pH=9.0 using acetic acid (10%). This gives the title compound in a yield of 75-80% of theory in a chemical purity of >98% and an optical purity of >99%.

10. (−)-5-Difluoromethoxy-2-[(3,4-dimethoxy-2-pyridinyl)methylsulphinyl]-1H-benzimidazole [=(−)-pantoprazole or (S)-pantoprazole] with (+)-L-tartaric acid bis-(N,N-pyrrolidinamide) and hafnium (IV) tert-butoxide At room temperature, 3.67 g of 5-difluoromethoxy-2-[(3,4-dimethoxy-2-pyridinyl)methylthio]-1H-benzimidazole, 4.10 g of (+)-L-tartaric acid bis-(N,N-pyrrolidinamide) and 2.60 ml of hafnium(IV) tert-butoxide are suspended in 18.5 ml of methyl isobutyl ketone. The mixture is heated at 40° C. for 1 hour, during which an almost clear solution is formed. After cooling to room temperature, 0.74 ml of N-ethyldiisopropylamine is added. 2.2 ml of cumene hydroperoxide are then slowly metered in. Stirring is continued at room temperature until the oxidation process has ended (48 hours, monitored by TLC). The clear solution is diluted with 20 ml of methyl isobutyl ketone and quenched with 0.3 g of sodium thiosulphate in 25 ml of saturated sodium bicarbonate solution and stirred for a further 14 hours. After phase separation, the methyl isobutyl ketone phase is washed two more times with 10 ml of saturated sodium bicarbonate solution. 30 ml of water are added to the methyl isobutyl ketone, phase and the pH is adjusted to 13 using 40% strength (w/w) aqueous sodium hydroxide solution. After phase separation, the methyl isobutyl ketone phase is once more extracted with 10 ml of water at pH=13. The aqueous phases are combined and, at 40° C. and under reduced pressure, subjected to incipient distillation. At 40-45° C., (−)-pantoprazole is precipitated by addition of 10% strength acetic acid to pH 9.0. Under pH control, stirring is continued for another 12 hours. The beige crystals are filtered off and washed with 10 ml of water. This gives the title compound in a yield of 2.5 g (65% of theory) in an optical purity of >95%. To increase the purity, (−)-pantoprazole is dissolved in water/aqueous sodium hydroxide solution at pH=13 and again precipitated at pH=9.0 using acetic acid (10%).

The invention claimed is:

1. A process for preparing (S)-pantoprazole in enantiomerically pure or enantiomerically enriched form comprising oxidizing 5-difluoromethoxy-2-[(3,4-dimethoxy-2-pyridinyl)methylthio]-1H-benzimidazole, wherein the oxidation is carried out in the presence of a chiral zirconium complex or a chiral hafnium complex.

2. A process for preparing (S)-pantoprazole in enantiomerically pure or enantiomerically enriched form comprising oxidizing 5-difluoromethoxy-2-[(3,4-dimethoxy-2-pyridinyl)methylthio]-1H-benzimidazole, wherein the oxidation is carried out in the presence of a chiral zirconium complex.

3. A process according to claim 1, wherein (S)-pantoprazole is obtained in an optical purity of >90%.

4. A process according to claim 1, wherein the oxidation is carried out using cumene hydroperoxide.

5. The process according to claim 1, wherein the chiral zirconium complex is selected from the group consisting of zirconium(IV) acetylacetonate, zirconium(IV) butoxide, zirconium(IV) tert-butoxide, zirconium(IV) ethoxide, zirconium(IV) n-propoxide, zirconium(IV) isopropoxide and zirconium(IV) isopropoxide/isopropanol, and wherein the chiral hafnium complex is selected from the group consisting of hafnium(IV) acetylacetonate, hafnium(IV) butoxide, hafnium(IV) tert-butoxide, hafnium(IV) ethoxide, hafnium (IV) n-propoxide, hafnium(IV) isopropoxide and hafnium (IV) isopropoxide/isopropanol.

6. The process according to claim 2, wherein the chiral zirconium complex is selected from the group consisting of zirconium(IV) acetylacetonate, zirconium(IV) butoxide, zirconium(IV) tert-butoxide, zirconium(IV) ethoxide, zirconium(IV) n-propoxide, zirconium(IV) isopropoxide and zirconium(IV) isopropoxide/isopropanol.

7. The process according to claim 1, wherein the oxidation is carried out in the presence of an organic base.

8. The process according to claim 1, wherein the oxidation is carried out in the presence of a tertiary amine.

9. The process according to claim 1, wherein the oxidation is carried out in an organic solvent.

10. The process according to claim 1, wherein the oxidation is carried out in an organic solvent comprising 0 to 0.3% by volume of water.

11. The process according to claim 1, wherein the oxidation is carried out in a solvent of commercially available quality.

12. The process according to claim 1, wherein the oxidation is carried out in an organic solvent which comprises methyl isobutyl ketone.

13. The process according to claim 1, wherein the oxidation is carried out in the presence of a chiral auxiliary.

14. The process according to claim 13, wherein the chiral auxiliary is a (+)-L-tartaric acid derivative.

15. The process according to claim 13, wherein the chiral auxiliary is selected from the group consisting of (+)-L-tartaric acid bis-(N,N-diallylamide), (+)-L-tartaric acid bis-(N,N-dibenzylamide), (+)-L-tartaric-acid bis-(N,N-diisopropylamide), (+)-L-tartaric acid bis-(N,N-dimethylamide), (+)-L-tartaric acid bis-(N-pyrrolidinamide), (+)-L-tartaric acid bis-(N-piperidinamide), (+)-L-tartaric acid bis-(N-morpholinamide), (+)-L-tartaric acid bis-(N-cycloheptylamide), (+)-L-tartaric acid bis-(N-4-methyl-N-piperazinamide), dibutyl (+)-L-tartrate, di-tert-butyl (+)-L-tartrate, diisopropyl (+)-L-tartrate, dimethyl (+)-L-tartrate and diethyl (+)-L-tartrate.

16. The process according to claim 13, wherein the chiral auxiliary is selected from the group consisting of (+)-L-tartaric acid bis-(N,N-dimethylamide), (+)-L-tartaric acid bis-(N-pyrrolidinamide) and (+)-L-tartaric acid bis-(N-morpholinamide).

17. The process according to claim 13, wherein the chiral zirconium complex is selected from the group consisting of zirconium(IV) acetylacetonate, zirconium(IV) butoxide, zirconium(IV) tert-butoxide, zirconium(IV) ethoxide, zirconium(IV) n-propoxide, zirconium(IV) isopropoxide, and zirconium(IV) isopropoxide/isopropanol, and wherein the chiral auxiliary is selected from the group consisting of (+)-L-tartaric acid bis-(N,N-diallylamide), (+)-L-tartaric acid bis-(N,N-dibenzylamide), (+)-L-tartaric acid bis-(N,N-diisopropylamide), (+)-L-tartaric acid bis-(N,N-dimethylamide), (+)-L-tartaric acid bis-(N-pyrrolidinamide), (+)-L-tartaric acid bis-(N-piperidinamide), (+)-L-tartaric acid bis-(N-morpholinamide), (+)-L-tartaric acid bis-(N-cycloheptylamide), (+)-L-tartaric acid bis-(N-4-methyl-N-piperazinamide), dibutyl (+)-L-tartrate, di-tert-butyl (+)-L-tartrate, diisopropyl (+)-L-tartrate, dimethyl (+)-L-tartrate and diethyl (+)-L-tartrate.

18. The process according to claim 13, wherein the chiral zirconium complex is selected from the group consisting of zirconium(IV) acetylacetonate, zirconium(IV) butoxide, zirconium(IV) tert-butoxide, zirconium(IV) ethoxide, zirconium(IV) n-propoxide, zirconium(IV) isopropoxide, and zirconium(IV) isopropoxide/isopropanol, and wherein the chiral auxiliary is selected from the group consisting of (+)-L-tartaric acid bis-(N,N-diallylamide), (+)-L-tartaric acid bis-(N,N-dibenzylamide), (+)-L-tartaric acid bis-(N,N-diisopropylamide), (+)-L-tartaric acid bis-(N,N-dimethylamide), (+)-L-tartaric acid bis-(N-pyrrolidinamide), (+)-L-tartaric acid bis-(N-piperidinamide), (+)-L-tartaric acid bis-(N-morpholinamide), (+)-L-tartaric acid bis-(N-cycloheptylamide), (+)-L-tartaric acid bis-(N-4-methyl-N-piperazinamide), dibutyl (+)-L-tartrate, di-tert-butyl (+)-L-tartrate, diisopropyl (+)-L-tartrate, dimethyl (+)-L-tartrate and diethyl (+)-L-tartrate, and wherein the oxidation is carried out in the presence of an organic base.

19. The process according to claim 13, wherein the chiral zirconium complex is selected from the group consisting of zirconium(IV) n-propoxide, zirconium(IV) isopropoxide and zirconium(IV) isopropoxide/isopropanol, and wherein the chiral auxiliary is selected from the group consisting of (+)-L-tartaric acid bis-(N,N-dimethylamide), (+)-L-tartaric acid bis-(N-pyrrolidinamide) and (+)-L-tartaric acid bis-(N-morpholinamide) and wherein the oxidation is carried out using cumene hydroperoxide.

20. The process according to claim 13, wherein the chiral zirconium complex is selected from the group consisting of used is zirconium(IV) n-propoxide, zirconium(IV) isopropoxide and zirconium(IV) isopropoxide/isopropanol, and wherein the chiral auxiliary is selected from the group consisting of (+)-L-tartaric acid bis-(N,N-dimethylamide), (+)-L-tartaric acid bis-(N-pyrrolidinamide) and (+)-L-tartaric acid bis-(N-morpholinamide) and wherein the oxidation is carried out using cumene hydroperoxide in the presence of a tertiary amine.

* * * * *